United States Patent [19]

Hartog et al.

[11] 4,163,060

[45] Jul. 31, 1979

[54] ARALKYLAMINO CARBOXYLIC ACIDS AND DERIVATIVES HAVING SPASMOLYTIC ACTIVITY

[75] Inventors: Jan Hartog; Johannes M. A. Zwagemakers, both of Weesp, Netherlands

[73] Assignee: U.S. Philips Corporation, New York, N.Y.

[21] Appl. No.: 759,798

[22] Filed: Jan. 17, 1977

Related U.S. Application Data

[62] Division of Ser. No. 564,789, Apr. 3, 1975, Pat. No. 4,034,103.

[30] Foreign Application Priority Data

Apr. 8, 1974 [NL] Netherlands .................. 7404732

[51] Int. Cl.² .................. A61K 31/275; C07C 101/16; C07C 103/28; C07C 121/78

[52] U.S. Cl. ..................... 424/278; 260/340.3; 260/340.5 R; 260/402.5; 260/404; 260/465 E; 260/558 A; 260/558 S; 260/559 A; 424/282; 424/304; 424/309; 424/318; 424/319; 424/324; 560/9; 560/38; 560/39; 562/431; 562/443; 562/444

[58] Field of Search ............... 560/38, 39; 260/465 E, 260/404, 558 A, 559 A, 340.3, 340.5 R, 518 R, 519; 562/443, 444; 424/304, 309, 318, 319, 324, 278, 282

[56] References Cited

U.S. PATENT DOCUMENTS

| | | | |
|---|---|---|---|
| 2,534,567 | 12/1950 | Baltzly et al. | 560/39 |
| 2,776,991 | 1/1957 | Surrey | 560/38 X |
| 3,689,524 | 9/1972 | Jack et al. | 260/570.8 R X |
| 3,886,195 | 5/1975 | Beregi et al. | 260/465 E |
| 4,015,011 | 3/1977 | Schromm et al. | 260/465 E |

*Primary Examiner*—Dolph H. Torrence
*Attorney, Agent, or Firm*—Norman N. Spain

[57] ABSTRACT

Novel substituted aromatic aliphatic amino carboxylic acids containing a tertiary nitrogen atom such as 3-[N-ethyl-[1-methyl-2-(4-methoxyphenyl)] ethylamino] -1-propane carboxylic acid ethyl ester or 7-[N-ethyl-[1-methyl-2-(4-methoxyphenyl)] ethylamino] -1-heptane carboxylic acid ethyl ester have been found to be useful spasmolytic agents.

28 Claims, 5 Drawing Figures

ARALKYLAMINO CARBOXYLIC ACIDS AND DERIVATIVES HAVING SPASMOLYTIC ACTIVITY

This is a division, of application Ser. No. 564,789, filed Apr. 3, 1975 U.S. Pat. No. 4,034,103.

The invention relates to spasmolytic compounds, to pharmaceutical compositions and to methods of preparing the compounds and the compositions.

The compound of formula 1

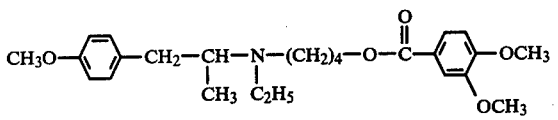

is known as a spasmolytic from Dutch Patent Specification No. 112,650. Upon oral administration, however, said compound has only a weak and short-lasting activity.

It is the object of the invention to provide compounds which have a specific spasmolytic activity on the smooth musculature of the tractus gastrointestinalis, the tractus urogenitalis and the bronchial system and which show said effect also for a long time and to a strong degree after oral administration.

It has been surprisingly found that novel compounds of formula 2:

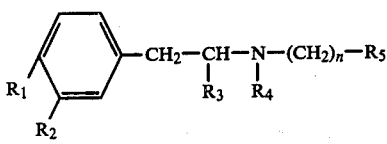

and their salts formed with pharmaceutically acceptable acids are significantly different from the compounds of formula 1 of said Dutch patent specification in regard to their properties in spite of the structural relationship between the compounds.

In Formula 2 the symbols have the following meanings: $R_1$ is an alkyl group, an alkoxy group, an alkylthio group or a dialkylamino group, which substituents have at most 2 carbon atoms, a hydroxy group, a hydrogen atom, a chlorine atom or a fluorine atom; $R_2$ is a hydrogen atom or, if $R_1$ represents a hydrogen atom, one of the remaining substituents summed up for $R_1$, while $R_1$ and $R_2$ both may be an alkoxy group having 1 or 2 carbon atoms or together represent a methylene dioxy or ethylene dioxy group; $R_3$ is an alkyl group having 1 or 2 carbon atoms; $R_4$ is an alkyl group having 1 to 3 carbon atoms; n is an integer number from 3 to 20 and $R_5$ is a group $COOR_6$, wherein $R_6$ represents a hydrogen atom, an ethyl group or a propyl group, a group $CONR_7R_7'$ wherein $R_7$ and $R_7'$ which are equal or different, each represent a hydrogen atom or an alkyl group having 1 to 3 carbon atoms, a group Cn on the understanding that when $R_6$ is a hydrogen atom, n should be larger than 5.

These new compounds have a strong spasmolytic activity on the smooth musculature of the tractus gastrointestinalis, the tractus urogenitalis and the bronchial system. Although said activity has a musculotropic and a neurotropic component, the compounds have no or substantially no peripheral parasympatholytic effects. The compounds exert their activity after parenteral and rectal administration and also after oral administration. Notably the oral activity is considerably stronger and longer than that of the compound of formula 1. This applies in particular to compounds of the invention in which $R_1=OCH_3$ and $R_2=H$.

A very strong activity was found in compounds in which n has the value 9 and $R_5$ represents a group $COOR_6$. The compounds of the invention in which $R_1=OCH_3$, $R_2=H$, $R_3=CH_3$, $R_4=C_2H_5$, n=9 and $R_5=COOC_2H_5$ and its salts, however, are to be preferred.

Because of their properties, the compounds after having been brought into a form suitable for administration, may be used for the treatment of all kinds of spastic diseases or of hypermotility of the smooth musculature of the tractus gastrointestinalis, the tractus urogenitalis and the broncial system, for example, for ureteral and renal colics, abdominal colics, colitis, postcholocystectomic syndrom, duodenal and ventricular ulcera, spastic colon, "irritable colon" and the like.

The dosage of the compounds to be administered depends on the nature and the severity of the disease to be treated. As a rule, when administered orally a quantity of 10 to 100 mg per time will be chosen. The compounds have a low toxicity. The $LD_{50}$ values for oral administration are as a rule above 500 mg/kg.

The dosage for oral use in animals is about 0.1 to 20 mg per kg body weight.

The spasmolytic activity of the compounds of formula 2 was measured inter alia in a test on starved guinea pigs of 500 to 700 gm. The animals were narcotised by intramuscular injection of 1.25 g/kg urethane. After the insertion of canules in the trachea and the vena jugularis, the abdomen was opened and an activily moving loop of the ileum was selected and tied off. The animals were placed in a bath containing Tyrode's solution at 37° C. in such manner that the abdomen was fully immersed. The tied-off part of the ileum was connected to a water manometer.

By means of a 20 ml syringe which was connected to the water manometer, the base pressure was adjusted at a value at which no spontaneous contractions occurred. Contractions were produced by administring 2.5 γ carbachol intravenously every 7 minutes. The contractions were recorded on a kymograph. After a constant response to the spasmogen had been obtained, a test compound wad administered intraduodenally. For that purpose a thin rubber catheter was inserted orally and connected in the duodenum.

Three minutes after the administration of the test compound, carbachol was injected. The administration of this spasmogen was repeated after every 7 minutes.

The contractions as a result of the spasmogen after administration of the test compound were expressed in percent of the contractions obtained prior to administration of the test compound. In this manner both the strength and the duration of the activity were determined.

The compounds of formula 2 and their salts can be obtained by means of methods which are known for the synthesis of this type of compounds and according to methods analogous thereto.

The invention also relates to a method of preparing new tertiary amines, characterized in that compounds of formula 2 in which the symbols have the above-described meanings and salts thereof formed with pharmaceutically acceptable acids are prepared according to methods which are known for the preparation of this type of compounds and according to methods analogous thereto.

The compounds can be obtained, for example, by reacting a compound of formula 3 Y₁—NH—Y₂ with a compound of formula 4 Hal Y₃. In these formulae, Y₁ represents either the group

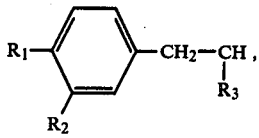

in which case Y₂ is the group —(CH₂)ₙ—R₅ and Y₃ is the group R₄, or conversely, or Y₁ is the group —(CH₂)ₙ—R₅, Y₂ is the group R₄ and Y₃ is the group

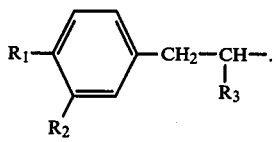

In formula 4, Hal is a halogen atom or a tosyloxy group, but preferably an iodine atom. The reaction is preferably carried out in an inert solvent, for example, acetonitrile, petroleum ether, benzene, toluene, acetone, methyl ethyl ketone, methanol and ethanol. The reaction mixture may comprise an acid binder, for example, a tertiary amine such as triethyl amine, pyridine and quinoline, an inorganic base, such as potassium carbonate or an excess of the amine of formula 3. The reaction temperature is between −20° and 200° C.

Acids of formula 2 can also be obtained by reacting a compound of formula 5

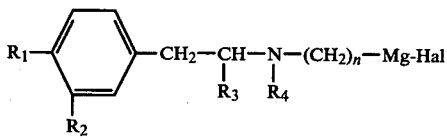

with carbon dioxide snow and decomposing the reaction product with dilute acid or by oxidation of an alcohol of formula 6

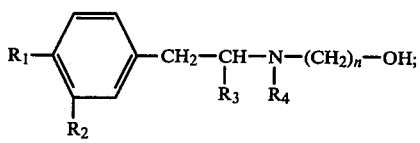

with, for example, potassium permanganate.

Acids obtained can be converted, if desired, into esters by a reaction with ethanol or propanol.

Esters can be converted into acids by acid or alkaline hydrolysis or into the amides by reaction with an amine NHR₇R₇'. This reaction can be carried out, for example, with an alcohol as a solvent and at temperatures between room temperature and the boiling point of the mixture.

As examples of pharmaceutically acceptable acids with which the amines according to the invention can form salts, may be mentioned: hydrochloric acid, hydrobromic acid, sulphuric acid, phosphoric acid, p.toluenesulfonic acid, benzoic acid, acetic acid, propionic acid, tartaric acid, succinic acid, citric acid, fumaric acid and maleic acid.

The compounds can be brought in a form suitable for administration by means of methods which are known per se. The compounds may be mixed with or dissolved in solid or liquid carrier materials. The resulting mixtures or solutions may be processed to pharmaceutical dosage unit forms, such as capsules, tablets, coated tablets, pills and suppositories.

The invention can be explained in greater detail with reference to the following Examples. If not stated to the contrary in the Examples, the compounds were obtained as a high-boiling-point oil, the boiling point of which could not be established as a result of decomposition. Nor was it possible in that case to obtain a crystallizing salt. The compounds were characterized by means of NMR-, IR and elementary analysis.

EXAMPLES (1) 3-[N-ethyl-[1-methyl-2-(4-methoxyphenyl)]-ethylamino]-1-propane carboxylic acid ethylester hydrochloride 62 g of sodium iodide were added to a solution of 139 g of N-ethyl-[1-methyl-2-(4-methoxyphenyl)]-ethylamine and 67.5 g of γ-bromobutyric acid ethylester in 650 ml of methyl ethyl ketone, after which the mixture was boiled under reflux while stirring for 65 hours. After cooling, the sodium bromide formed was sucked off after which the filtrate was concentrated until substantially no solvent was present any longer. The residue was dissolved in 1 l of diethylether and 1 l of water. After draining the water layer, the ether layer was washed another two times with 250 ml of water. The ether extract was then washed with 2 N hydrochloric acid (3×300 ml). The acid extract was rendered alkaline (pH 8) with concentrated ammonia and the oil which separated was taken up in ether (3×250 ml). The resulting solution of the desired tertiary amine and the secondary amine which was started from was washed with 25 ml of 2 N hydrochloric acid. This was repeated so often as was necessary to remove all the starting amine. Then there was dried on sodium sulphate and evaporated to dryness. 5 g of the pure base obtained in this manner were converted into the hydrochloride with 3 N ethanolic hydrochloric acid (5 ml). The resinous product which remained after removing the ethanol was crystallised from a mixture of acetone and ether (1 vol:20 vol). Melting point 94°–96° C.

(2) 5-[N-ethyl-[1-methyl-2-(4-methoxyphenyl)]-ethylamino-1-pentane carboxylic acid ethylester A mixture of 13 g of N-ethyl-[1-methyl-2-(4-methoxyphenyl)]ethylamine, 6.8 g of triethylamine, 15.5 g of ω-bromocapronic acid ethylester and 10.1 g of sodium iodide in 100 ml of methyl ethyl ketone was boiled under reflux for 64 hours while stirring. After cooling, filtering and concentrating the resulting filtrate, the residue was taken up in 200 ml of ether and 100 ml of water. After separating the water layer, the ether was extracted another two times with 50 ml of water. The ether extract was then washed with three times 50 ml of 2 N hydrochloric acid, after which said acid extract was rendered alkaline with concentrated ammonia. The formed base was taken up in ether (3×50 ml). After drying on sodium sulphate and evaporation to dryness the title compound was obtained as an oil. In a manner analogous to that described in Example 2 were obtained:

(3) 6-[N-ethyl-[1-methyl-2-(4-methoxyphenyl)]ethylamino]-1-hexane carboxylic acid ethylester hydrochloride. Melting point 91°–93° C.

(4) 7-[N-ethyl-[1-methyl-2-(4-methoxyphenyl)]ethylamino]-1-heptanecarboxylic acid ethyl ester.

(5) 9-[N-ethyl-[1-methyl-2-(4-methoxyphenyl)]ethylamino]-1-nonane carboxylic acid ethylester hydrochloride. Melting point 51°–52° C.

(6) 10-[N-ethyl-[1-methyl-2-(4-methoxyphenyl)]ethylamino]-1-decane carboxylic acid ethylester hydrochloride. Melting point 59°–61° C.

(7) 15-[N-ethyl-[1-methyl-2-(4-methoxyphenyl)]ethylamino]-1-pentadecane carboxylic acid ethylester hydrochloride. Melting point 52°–54° C.

(8) 3-[N-ethyl-[1-methyl-2-(3-methoxyphenyl)]ethylamino]-1-propane carboxylic acid ethylester.

(9) 3-[N-ethyl(1-methyl-2-phenyl)ethylamino]-1-propanecarboxylic acid ethylester.

(10) 3-[N-ethyl-[1-methyl-2-(4-methylphenyl)]ethylamino]-1-propane carboxylic acid ethylester hydrochloride. Melting point 94°–95° C.

(11) 3-[N-ethyl-[1-methyl-2-(4-chlorophenyl)]ethylamino]-1-propane carbonic acid ethylester.

(12) 3-[N-ethyl-[1-methyl-2-(4-dimethylaminophenyl)-]ethylamino]-1-propane carboxylic acid ethylester.

(13) 3-[N-ethyl-[1-methyl-2-(3,4-dimethoxyphenyl)]ethylamino]-1-propane carboxylic acid ethylester.

(14) 3-[N-ethyl-[1-methyl-2-(4-methoxyphenyl)]ethylamino]-1-propane carboxylic acid n-propyl ester hydrochloride. Melting point 97°–99° C.

(15) 3-[N-ethyl-[1-methyl-2-(4-methoxyphenyl)]ethylamino]-1-propane carboxylic acid i-propylester hydrochloride. Melting point 132°–133° C.

(16) 3-[N-methyl-[1-methyl-2-(4-methoxyphenyl)]ethylamino]-1-propane carboxylic acid ethylester.

(17) 3-[N-propyl-[1-methyl-2-(4-methoxyphenyl)]ethylamino]-1-propane carboxylic acid ethylester.

(18) 4-[N-ethyl-[7-methyl-2-(4-methoxyphenyl)]ethylamino]-butyronitrile.

(19) 5-[N-ethyl-[1-methyl-2-(4-methoxyphenyl)]ethylamino]-valeronitrile hydrochloride. Melting point 128°–130° C.

(20) 4-[N-ethyl-[1-methyl-2-(4-methoxyphenyl)]ethylamino]-butyl methyl sulphone.

(21) 9-[N-ethyl-[1-methyl-2-(4-methoxyphenyl)]ethylamino]-1-nonane carboxylic acid hydrochloride.

A mixture of 11.5 g of 9-[N-ethyl-[1-methyl-2-(4-methoxy-phenyl)]ethylamino]-1-nonane carbonic acid ethyl ester, 5.6 g of potassium carbonate, 320 ml of ethanol and 18.5 ml of water was boiled under reflux for 60 hours and then concentrated under reduced pressure until it was substantially free from solvent. The residue was taken up in 100 ml of ether and 100 ml of water. After separating the water layer, same was neutralised with concentrated hydrochloric acid (to pH 6.5) and the precipitated acid was extracted with methylene chloride (3×50 ml). After drying and evaporating to dryness of the extract, 10.4 g of acid were obtained which was converted into the hydrochloride with 3.4 N ethanolic hydrochloric acid. After evaporating the ethanol, the residue was crystallised from acetone. Melting point 84°–86° C. In analogous manners were obtained:

(22) 6-[N-ethyl-[1-methyl-2-(4-methoxyphenyl)]ethylamino]-1-hexane carboxylic acid hydrochloride. Melting point 123°–124° C.

(23) 7-[N-ethyl-[1-methyl-2-(4-methoxyphenyl)]ethylamino]-1-heptane carboxylic acid hydrochloride. Melting point 118°–120° C.

(24) 10-[N-ethyl-[1-methyl-2-(4-methoxyphenyl)]ethylamino]-1-decane carboxylic acid.

(25) 4-[N-ethyl-[1-methyl-2-(4-methoxyphenyl)]ethylamino]-butyramide.

6 g of 4-[N-ethyl-[1-methyl-2-(4-methoxyphenyl)]ethylamino]butyric acid ethylester were dissolved in 300 ml of methanol which was saturated with ammonia at 0° C. The mixture was transferred to an autoclave and shaken at 40° C. for one week. The solvent and the reagent were then removed and the resulting residue was purified over 50 g of silicagel with mixtures of methylene chloride and acetone as eluents. In this manner the title compound was obtained in a pure form.

In an analogous manner was obtained with methyl amine instead of ammonia:

(26) N-methyl-4-[N-ethyl-[1-methyl-2-(4-methoxyphenyl)]-ethylamino]-butyramide.

With dimethyl amine instead of ammonia was obtained in an analogous manner:

(27) N,N-dimethyl-4-[N-ethyl-[1-methyl-2-(4-methoxyphenyl)]-ethylamino]-butyramide.

As examples of pharmaceutical compositions may be mentioned:

(28) Capsules containing
  25 mg of active substance
  25 mg of lactose
  0.5 mg of polyvinyl pyrrolidon
  4.0 mg of carboxymethyl cellulose
  1.0 mg of magnesium stearate.

(29) Tablets having the composition as stated in Example 28.

(30) Suppositories containing
  10 mg of active substance
  1490 mg of oleum cacao.

(31) Injection liquid containing
  10 mg of active substance
  15 mg of benzyl alcohol
  pyrogen-free distilled water to 1 ml.

What is claimed is:

1. Compounds of of the formula 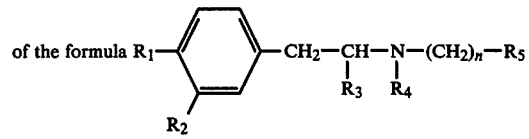

wherein $R_1$ is an alkyl group, an alkoxy group, an alkylthio group or a dialkylamino group, which substituents have up to 2 carbon atoms, a hydroxy group, a hydrogen atom, a chlorine atom or a fluorine atom, $R_2$ is a hydrogen atom or, if $R_1$ is a hydrogen atom, one of the remaining substituents summed up for $R_1$, while $R_1$ and $R_2$ both may be an alkoxy group having 1 or 2 carbon atoms or together a methylene dioxy group or ethylene dioxy group; $R_3$ is an alkyl group having 1 or 2 carbon atoms; $R_4$ is an alkyl group having 1 to 3 carbon atoms; n is an integer from 3 to 20 and $R_5$ is a group $COOR_6$, wherein $R_6$ is a hydrogen atom, an ethyl group or a propyl group, a group $CONR_7R_7'$, wherein $R_7$ and $R_7'$ which may be equal or different, each is a hydrogen atom or an alkyl group having 1 to 3 carbon atoms or a group CN providing that when $R_6$ is a hydrogen atom, n is larger than 5 and salts thereof formed with pharmaceutically acceptable acids.

2. A compound of claim 1 which is 3-[N-ethyl-[1-methyl-2-(4-methoxyphenyl)]ethylamino]-1-propane carboxylic acid ethyl ester and salts thereof formed with pharmaceutically acceptable acids.

3. A compound of claim 1 which is 6-[N-ethyl-[1-methyl-2-(4-methoxyphenyl)]ethylamino]-1-hexane carboxylic acid ethylester and its salts.

4. A compound of claim 1 which is 7-[N-ethyl-[1-methyl-2-(4-methoxyphenyl)]ethylamino]-1-heptane carboxylic acid ethylester and its salts.

5. A compound of claim 1 which is 9-[N-ethyl-[1-methyl-2-(4-methoxyphenyl)]ethylamino-1-nonane carboxylic acid ethylester and its salts.

6. A compound of claim 1 which is 10-[N-ethyl-[1-methyl-2-(4-methoxyphenyl)]ethylamino]-1-decane carboxylic acid ethylester and its salts.

7. A compound of claim 1 which is 15-[N-ethyl[1-methyl-2-(4-methoxyphenyl)]ethylamino]-1-pentadecane carboxylic acid ethylester and its salts.

8. A compound of claim 1 which is 3-[N-ethyl-[1-methyl-2-(3-methoxyphenyl)]ethylamino]-1-propane carboxylic acid ethylester and its salts.

9. A compound of claim 1 which is 3-[N-ethyl-(1-methyl-2-phenyl)ethylamino]-1-propane carboxylic acid ethylester and its salts.

10. A compound of claim 1 which is 3-[N-ethyl-[1-methyl-2-(4-methylphenyl)]ethylamino]-1-propane carboxylic acid ethylester and its salts.

11. A compound of claim 1 which is 3-[N-ethyl-[(1-methyl-2-(4-dimethylamino-phenyl)]-ethylamino]-1-propane carboxylic acid ethylester and its salts.

12. A compound of claim 1 which is 3-[N-ethyl-[(1-methyl-2-(4-chlorophenyl)]ethylamino]-1-propane carboxylic acid ethylester and its salts.

13. A compound of claim 1 which is 3-[N-ethyl-[1-methyl-2-(3,4-dimethoxyphenyl)]ethylamino]-1-propane carboxylic acid ethylester and its salts.

14. A compound of claim 1 which is 3-[N-ethyl-[1-methyl-2-(4-methoxyphenyl)]ethylamino]-1-propane carboxylic acid n. propylester and its salts.

15. A compound of claim 1 which is 3-[N-ethyl-[1-methyl-2-(4-methoxyphenyl)]ethylamino]-1-propane carboxylic acid ipropylester and its salts.

16. A compound of claim 1 which is 3-[N-propyl-[1-methyl-2-(4-methoxyphenyl)]ethylamino]-1-propane carboxylic acid ethylester and its salts.

17. A compound of claim 1 which is 4-[N-ethyl-[1-methyl-2-(4-methoxyphenyl)]ethylamino]-butyronitrile and its salts.

18. A compound of claim 1 which is 5-[N-ethyl-[1-methyl-2-(4-methoxyphenyl]ethylamino]-valeronitrile and its salts.

19. A compound of claim 1 which is 9-[N-ethyl-[1-methyl-2-(4-methoxyphenyl)]ethylamino]-1-nonane carboxylic acid and its salts.

20. A compound of claim 1 which is 6-[N-ethyl-[1-methyl-2-(4-methoxyphenyl)]ethylamino]-1-hexane carboxylic acid and its salts.

21. A compound of claim 1 which is 7-[N-ethyl-[1-methyl-2-(4-methoxyphenyl)]ethylamino]-1-heptane carboxylic acid and its salts.

22. A compound of claim 1 which is 10-[N-ethyl-[1-methyl-2-(4-methoxyphenyl)]ethylamino]-1-decane-carboxylic acid and its salts.

23. A compound of claim 1 which is 4-[N-ethyl[1-methyl-2-(4-methoxyphenyl)]ethylamino]-butyramide and its salts.

24. A compound is claim 1 which is N-methyl-4-[N-ethyl-[1-methyl-2-(4-methoxy-phenyl)]ethylamino]-butyramide and its salts.

25. A compound of claim 1 which is N,N-dimethyl-4-[N-ethyl[1-methyl-2-(4-methoxy-phenyl)]ethylamino]-butyramide and its salts.

26. A spasmolytic composition comprising, in a spasmolytically effective amount, a compound of claim 1 and a pharmaceutically acceptable carrier therefor.

27. A method of providing spasmolytic therapy to a patient in need thereof comprising administering to said patient a spasmolytically effective amount of the composition of claim 26.

28. The method of claim 27 wherein the administration is by the oral route.

* * * * *